United States Patent [19]

Palusamy et al.

[11] Patent Number: 4,935,195
[45] Date of Patent: Jun. 19, 1990

[54] CORROSION-EROSION TREND MONITORING AND DIAGNOSTIC SYSTEM

[75] Inventors: Sam S. Palusamy, Murrysville; John C. Schmertz, Pittsburgh; David H. Roarty, Murrysville, all of Pa.

[73] Assignee: Westinghouse Electric Corp., Pittsburgh, Pa.

[21] Appl. No.: 237,537

[22] Filed: Aug. 29, 1988

[51] Int. Cl.$^5$ .............................................. G21C 17/00
[52] U.S. Cl. ........................................ 376/249; 73/592
[58] Field of Search ...................... 376/249, 305, 215; 73/570, 592

[56] References Cited

U.S. PATENT DOCUMENTS

| | | | |
|---|---|---|---|
| 4,060,716 | 11/1977 | Pekrul et al. | 376/216 |
| 4,184,205 | 1/1980 | Morrow | 364/508 |
| 4,393,711 | 7/1983 | Lapides | 73/592 |
| 4,655,077 | 4/1987 | Purvis et al. | 73/86 |
| 4,764,882 | 8/1988 | Braschel | 376/249 |

FOREIGN PATENT DOCUMENTS 0170516 2/1986 European Pat. Off. .
2312060 12/1976 France .

OTHER PUBLICATIONS

"Corrosion Monitoring System Provides Fast Measurements," *Instrumentation and Control Systems*, vol. 56, No. 8, p. 53, Aug. 1983.
"Managing Erosion/Corrosion with the WATHEC Code," *Nuclear Engineering International*, vol. 34, No. 418, May 1989, pp. 18-20.
"CMS Records Transient Data and Performs On-Line Analysis," *Nuclear Engineering International*, vol. 32, No. 396, Jul. 1987, pp. 44, 45.
European Search Report, Dec. 12, 1989, Berlin.
NRC Bulletin No. 87-01: Thinning of Pipe Walls in Nuclear Power Plants; Jul. 9, 1987, pp. 1-3, U.S. Nuclear Regulatory Commission, Office of Nuclear Reactor Regulation, Washington, D.C.
NRC Information Notice No. 88-17: Summary of Responses to NRC 87-01, "Thinning of Pipe Walls in Nuclear Power Plants"; Apr. 22, 1988, pp. 1-5 (with 3 attachments), U.S. Nuclear Regulatory Commission, Office of Nuclear Reactor Regulation, Washington, D.C.

Primary Examiner—Donald P. Walsh
Attorney, Agent, or Firm—E. F. Possessky

[57] ABSTRACT

A system for analyzing containment integrity of a containment system includes data storage for inspection data and characteristic data and a data evaluation processor for evaluating the inspection data. A data acquisition system is used for periodically obtaining wall thicknesses of selected components in the containment system. After data validation, the actual wall thicknesses are stored as the inspection data in the data storage. The data evaluation processor analyzes the present pipe wall integrity in light of stress calculated from the characteristic data including operational conditions and material properties. In addition, the data evaluation processor analyzes the trend in change of wall thickness to forecast future wall thicknesses.

15 Claims, 3 Drawing Sheets

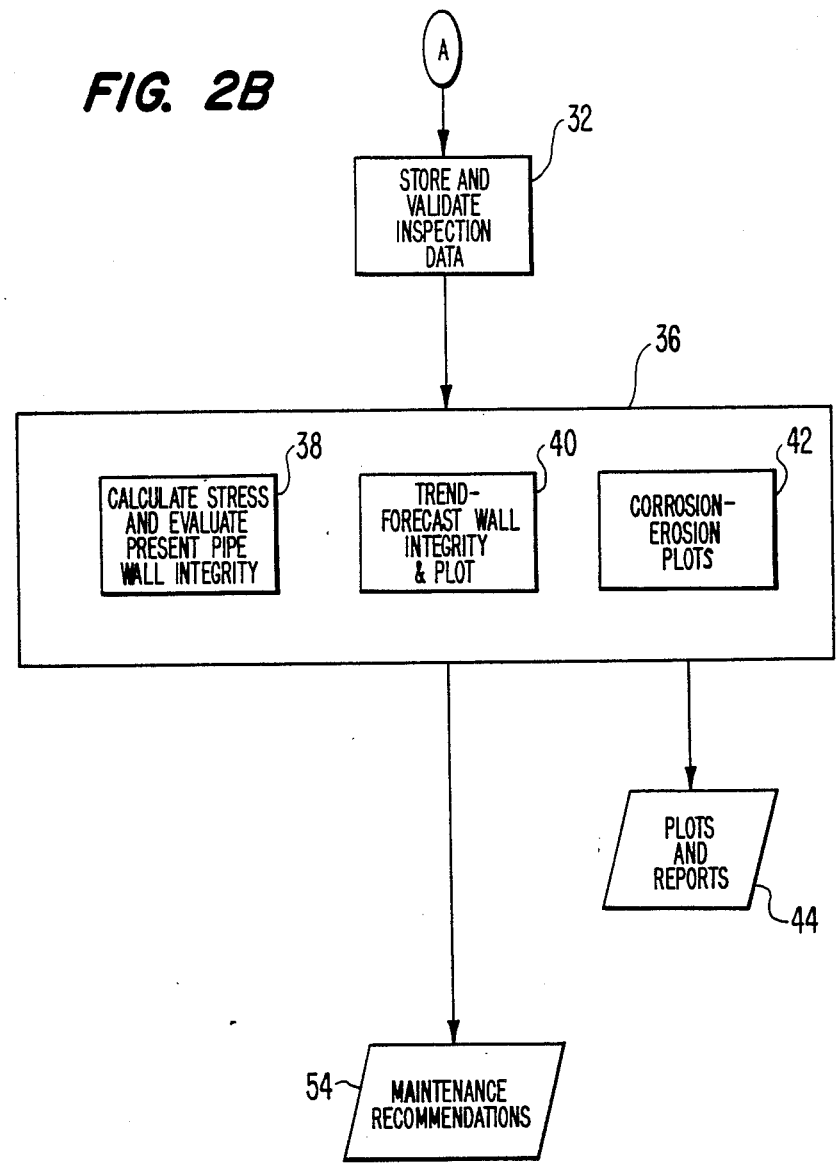

CORROSION-EROSION TREND MONITORING AND DIAGNOSTIC SYSTEM

BACKGROUND OF THE INVENTION

1. Field of the Invention

The present invention is related to the monitoring of erosion and corrosion in components of a containment system and, more particularly, to a system for monitoring wall thinning of pipes in a nuclear reactor due to corrosion and erosion.

2. Description of the Related Art

Any system of pipes, or more generally any containment system for containing flowing fluids, is subject to both corrosion and erosion which cause wall thinning. When the fluid is itself hazardous, e.g., toxic, radioactive, etc., or when loss of fluid is hazardous, e.g., in the cooling system of the nuclear reactor, maintaining containment integrity in the system is extremely important. Typically, such systems operate under pressure and if the wall thinning proceeds far enough, such walls can rupture causing loss of the fluid and resulting hazards.

As nuclear powered electricity generating plants have aged, wall thinning at plants has become an increasing concern of the Nuclear Regulatory Commission (NRC) which issued a bulletin on Jul. 9, 1987 requesting information regarding existing programs for avoiding detrimental effects from pipe wall thinning. NRC Informational Notice 88-17 dated Apr. 22, 1988 reported a summary of the response to the July 1987 request. According to this Notice, inspection programs existing at all plants surveyed indicate that corrosion or erosion exists at all plants and that feedwater condensate and recirculation systems are the most severely affected. According to the NRC April 1988 Notice, none of the plants responding to the July 1987 include systematic evaluations of the inspection data.

SUMMARY OF THE INVENTION

An object of the present invention is to enable management of massive amounts of data collected during corrosion-erosion monitoring of piping systems.

Another object of the present invention is to enable assessment of corrosion-erosion data in an efficient manner.

Yet another object of the present invention is to provide recommendations on maintenance of equipment subjected to corrosion and erosion to maintain containment integrity.

The above objects are attained by providing a method of assessing containment integrity, comprising the steps of: storing characteristic data for at least one component of a containment system to be monitored, storing inspection data for the at least one component and automatically evaluating the inspection data based on the characteristic data to produce an assessment of the containment integrity of the at least one component. The method preferably includes periodically measuring actual wall thickness of selected components to obtain the inspection data and analyzing the inspection data and characteristic data, including nominal wall thickness, to determine a trend in change of the actual wall thickness. This trend in wall thickness change is preferably used to produce a prioritized indication of maintenance for the inspected component.

The invention may be embodied in a system for assessing containment integrity, comprising storage means for storing characteristic data and inspection data for at least one component of a containment system to be monitored, acquisition means for acquiring the inspection data including actual wall thickness of the at least one component and evaluation means for automatically evaluating the inspection data based on the characteristic data to produce an assessment of the containment integrity of the at least one component.

These objects, together with other objects and advantages which will be subsequently apparent, reside in the details of construction and operation as more fully hereinafter described and claimed, reference being had to the accompanying drawings forming a part hereof, wherein like reference numerals refer to like parts throughout.

BRIEF DESCRIPTION OF THE DRAWINGS

FIGS. 2A and 2B are a flowchart of a method for assessing containment integrity according to the present invention.

DESCRIPTION OF THE PREFERRED EMBODIMENTS

In a typical nuclear powered electricity generating plant there are hundreds of components which contain fluid. Such components include piping systems with elbows, tees, reducers, flanges and other fittings, tanks, valves, etc. Many other types of piping systems, have similar complexity, such as petrochemical plants. Management of the massive amounts of data required to evaluate containment integrity of such complex systems is greatly facilitated by using an automated system like that illustrated in FIG. 1. Such a system is preferably operated in accordance with the flowchart illustrated in FIGS. 2A and 2B.

Attempting to monitor all portions of complex containment systems using existing and foreseeable future technology would be prohibitively expensive. Therefore, the first step in monitoring containment integrity is to locate potential weak points within the system. This can be done using a combination of design knowledge, experience and testing. The Electrical Power Research Institute (EPRI), for instance, has developed a program called CHEC which can be used to help identify piping systems which are most likely to be subjected to corrosion and erosion. This program uses flow rate, temperature and other applicable properties, to aid in determining the location of components to be monitored. As plants with similar designs grow older, maintenance records for one plant can be used to predict systems to be monitored at other plants. In addition, investigation into the causes of corrosion and erosion requiring repair or replacement of components may help identify components to be monitored.

Figure 2A:
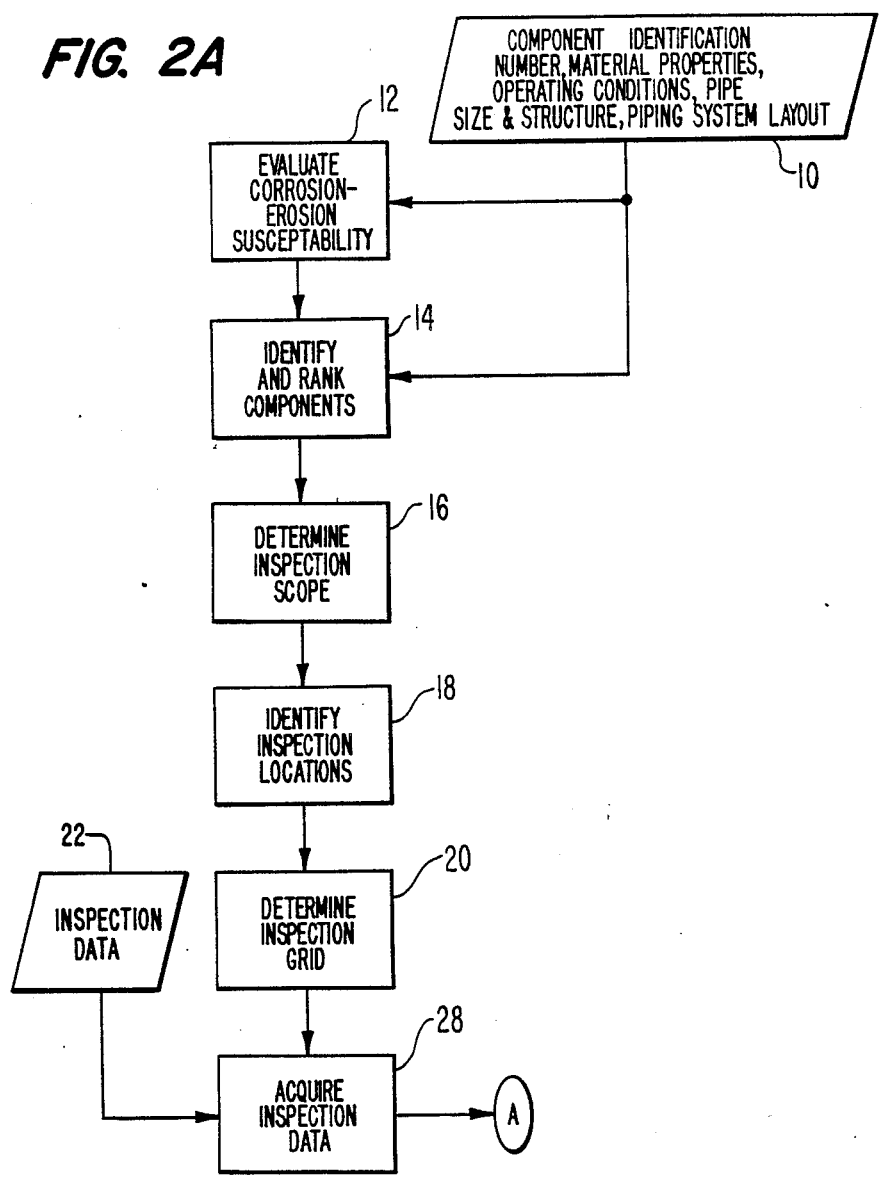

Thus, as illustrated in FIG. 2A, the first step in a method according to the present invention is to input system, component and location data 10, such as a component identification number, material properties, operating conditions, pipe size, a description of component structure and piping system layout. This data is used to evaluate corrosion-erosion susceptibility 12 and to identify and rank components 14. Then, plant personnel determine inspection scope 16 based upon the information provided in steps 12 and 14 taking into consideration the cost of monitoring and storing inspection data compared to the benefits derived based upon the likelihood of loss and containment integrity of a component resulting from corrosion-erosion.

Once the components to be inspected have been selected, it is necessary to identify the locations 18 where the wall thickness of the components will be measured. Preferably, ultrasonic testing with, e.g., a Krautkramer Branson DME hand held ultrasonic thickness gauge, is performed to measure the wall thickness of the components. Use of hand held units of this type provide substantial savings over permanently mounted sensors in typical applications. In applications where wall thickness may change quickly or an extremely critical component is being monitored, permanently mounted sensors could be used to provide continuous monitoring. Regardless of what type of sensors are used, the wall thickness of a component is preferably measured using a three-dimensional inspection grid which must be determined 20 for each type of component. In the case of a pipe for example, the inspection grid may consist of several cross-sections spaced along the pipe with, e.g., 10–20 points spaced around the circumference of the pipe at each cross-section. The grid is generally specified in an alpha-numeric fashion, i.e., A1, A2, where one parameter represents a point in the circumferential direction and the other parameter would represent points in the axial direction. This yields a matrix of data in a format convenient for storage, plotting, and evaluation. For components which deviate significantly from a pipe, e.g. a branch or tee, two or more matrices would be applied to completely cover the component.

Figure 1:
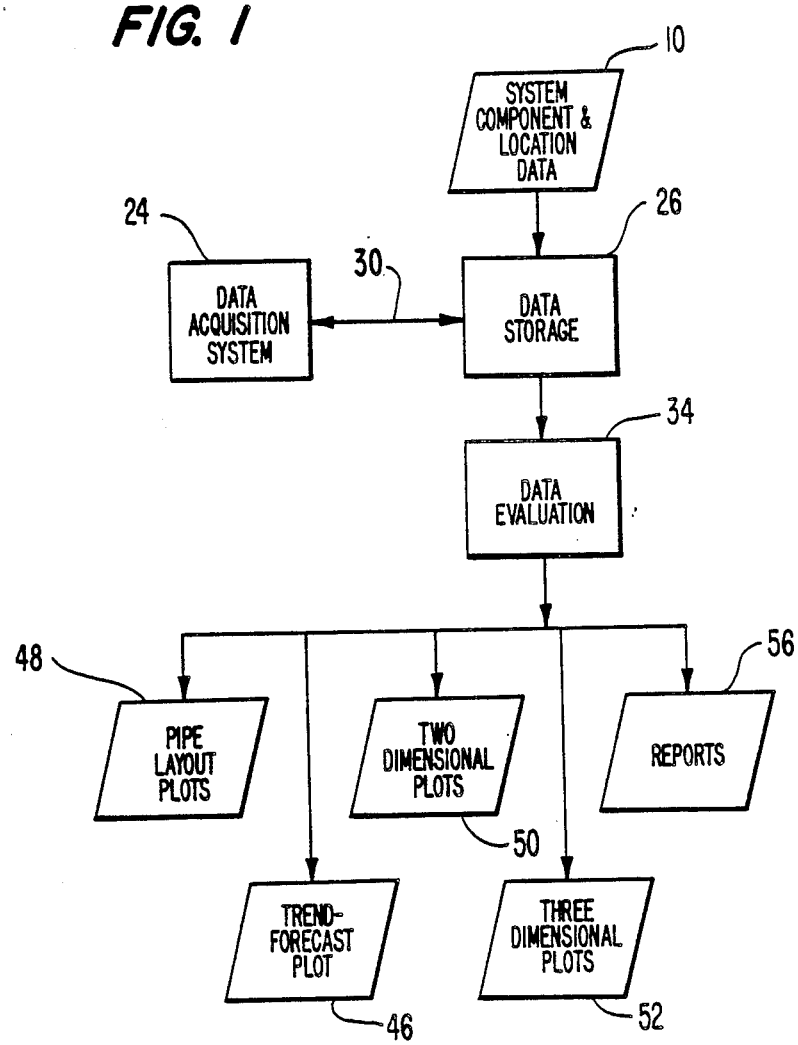
FIG. 1 is a block diagram of a system according to the present invention.

After steps 10, 12, . . . , 20 are completed, inspection of the components can begin so that inspection data can be input 22 into the hand held ultrasonic testers. The ultrasonic testers are part of the data acquisition system 24 (FIG. 1) which provide the inspection data that is stored with system, component and location data 10 in data storage 26. The operation of the data acquisition system 24 is illustrated in FIG. 2A as the acquiring of inspection data 28. As indicated in FIG. 1 by the double-headed arrow 30 between the data acquisition system and data storage 26, the component identification number can be provided to individuals to form an inspection schedule for the containment system. Some hand held ultrasonic testing units have the capability to store and display the location to be tested. Where hand held equipment is used which is not capable of performing this function, a printout or other form of output can be used to inform the inspectors where to measure wall thickness. The component identification number on a printout or stored in a testing unit can be compared with an inspection identifier located at the site of the component to be measured. The person performing the inspection inputs the inspection identifier when measuring each component. If the hand held ultrasonic tester includes a bar code reader or similar means for inputting the inspection identifier, the possibility of error in manually recording the inspection identifier can be reduced.

The data acquisition system 24 also includes means for storing the inspection data in the data storage 26. Where hand held ultrasonic testers are used, the data acquisition system includes a processor capable of uploading the inspection data from the ultrasonic testers. Where permanent sensors are used, the data acquisition system 24 would include the necessary cabling to connect the sensors to the data storage 26 and means for performing all necessary signal conditioning and processing. Regardless of the type of sensors used for obtaining the inspection data, the inspection data is stored in the data storage 26 at locations determined in dependence upon the inspection identifiers from the data acquisition system 24 and the component identification numbers previously stored in data storage 26. The inspection data is preferably acquired periodically with the frequency of inspection of each component determined by the expected rate of corrosion-erosion and the criticality of the function performed by the component.

The first step in processing the data acquired by the data acquisition system 24 is to validate 32 the inspection data. This data validation is preferably performed when the data is stored so that there is an immediate indication of inspection data that is invalid or close to minimum tolerance of a component. In addition, a data evaluation processor 34 may be used to compare the inspection data with predetermined ranges to determine validity of the inspection data and locations of excessive wall thinning. In addition, the data evaluation processor 34 (FIG. 1) performs data evaluation 36 (FIG. 2B) including evaluation of present integrity 38, trend analysis and forecast of wall integrity 40 and production 42 of corrosion-erosion plots all output as plots and reports 44.

Using the most recently acquired actual wall thickness data, the data evaluation processor 34 evaluates the present pipe wall integrity 38 (FIG. 2B). This evaluation 38 may include calculating stress on a component in dependence upon characteristic data, such as material properties, operating conditions, pipe size and structure of the component. The accuracy of the evaluation 38 of present pipe wall integrity will vary depending upon the accuracy of the calculation of stress which may be any known method for calculation of stress that provides a reasonably accurate evaluation of pipe wall integrity. The pipe wall integrity can then be evaluated in dependence upon the actual wall thickness most recently measured, material properties and component structure and the stress calculated using known methods to determine the ability of the remaining structure of the component to contain fluids at the pressure indicated by the operating conditions.

A system according to the present invention goes beyond evaluation of present pipe wall integrity by analyzing the inspection data recorded over a period of time for a component in light of the characteristic data to determine a trend in change of the actual wall thickness. Preferably, this analysis includes extrapolating from the stored inspection data using, e.g , a curve fitting algorithm or a corrosion-erosion rate based upon previous experience in similar systems or analysis of other factors, such as local fluid velocity, local fluid turbulence, fluid chemistry, piping materials and electrical power demand on nearby pumps. The preferred method for outputting the forecast of containment integrity is in the form of a plot 44 indicating when the wall of the component can be expected to become dangerously thin.

Depending upon the amount of inspection data, the length of time the plant has operated when the analysis is performed, the length of time since the last analysis was performed, the relative importance of evaluating present pipe wall integrity or performing trend analysis on the data can vary. Therefore, the different forms of analysis performed in data evaluation 36 are preferably selectable interactively by an operator of the system.

Included among the options which are preferably available to the operator is a variety of plots 42 of the data stored and analysis performed by the system. These plots are indicated in general in FIG. 2B as plots and reports 44 and in more detail in FIG. 1. The trend-forecast plot 46 is output from trend analysis 40. A variety of pipe layout plots 48 can be provided to aid in locating components to be inspected, to verify the accuracy of the input data and to aid in locating components in need of repair. Two-dimensional 50 and three-dimensional 52 plots are preferably provided to provide a graphical representation of corrosion-erosion within a component, thereby providing an indication of the degree of urgency for repair or replacement of the component.

Similarly, maintenance recommendations 54 (FIG. 2B) and other reports 56 (FIG. 1) are output based upon the types of data evaluation selected by the operator. The maintenance recommendations 54 preferably include a prioritized indication of maintenance required on the component being monitored. The automatic production of maintenance recommendations provides a significant advantage over manual analysis of the large mass of data required to analyze even a few selected components.

Many features and advantages of the present invention are apparent from the detailed specification and thus, it is intended by the appended claims to cover all such features and advantages of the system which fall within the true spirit and scope of the invention. Further, since numerous modifications and changes will readily occur to those skilled in the art, it is not desired to limit the invention to the exact construction and operation illustrated and described. Accordingly, all suitable modifications and equivalents may be resorted to falling within the scope and spirit of the invention.

What is claimed is:

1. A method of assessing wall thinning rate of a containment system containing a substance and subject to erosion and corrosion, comprising the steps of:
   (a) storing characteristic data for at least one component of the containment system to be monitored;
   (b) storing inspection data for the at least one component; and
   (c) automatically evaluating the inspection data based on the characteristic data to produce an assessment of the wall thinning rate of the at least one component.

2. A method as recited in claim 1,
further comprising the steps of:
   (d) measuring actual wall thickness of the at least one component to obtain the inspection data; and
   (e) repeating steps (b) and (d) periodically,
   wherein step (a) comprises the step of (ai) storing nominal wall thickness as part of the characteristic data, and
   wherein step (c) comprises the step of (ci) analyzing the inspection data and characteristic data too determine a trend in change of the actual wall thickness.

3. A method as recited in claim 2, wherein the containment system includes a piping system,
   wherein step (a) further comprises the step of (aii) storing at least one of a component identification number, a description of component structure, pipe size, material properties and operating conditions as the characteristic data.

4. A method as recited in claim 3, further comprising the step of (f) automatically selecting the at least one component from among all components of the containment system in dependence upon susceptibility to corrosion and erosion and a predicted rate of corrosion-erosion.

5. A method as recited in claim 4,
   wherein step (f) includes automatically selecting a plurality of components in the containment system as the at least one component,
   wherein step (a) further comprises the step of (aiii) storing an inspection grid and a component location as part of the characteristic data for each of the components selected in step (f), and
   wherein said measuring in step (d) is performed on the component selected in step (f) in accordance with the inspection grid stored in step (a) for a corresponding component.

6. A method as recited in claim 5,
further comprising the step of (g) storing an inspection identifier for each of the components measured in step (b) when said measuring of the corresponding component occurs, and
   wherein step (b) comprises storing the inspection data at locations determined in dependence upon the inspection identifier stored in step (g) and the component identification number stored in step (a).

7. A method as recited in claim 3, wherein step (c) further comprises the steps of:
   (cii) comparing the inspection data with predetermined ranges to determine validity of the inspection data and locations of excessive wall thinning;
   (ciii) calculating stress on the at least one component in dependence upon the characteristic data; and
   (civ) evaluating the containment integrity of the at least one component in dependence upon the actual wall thickness most recently measured in step (d) and the stress calculated in step (ciii).

8. A method as recited in claim 7, wherein step (ci) comprises extrapolating from the inspection data stored during completed repetitions of step (b) using one of a curve fitting algorithm and a predetermined corrosion-erosion rate.

9. A method as recited in claim 8, further comprising the step of (h) plotting predicted wall thickness of the at least one component.

10. A method as recited in claim 2, further comprising the step of (f) plotting the inspection data to produce a graphical representation of wall thinning within the at least one component.

11. A method as recited in claim 2, further comprising the step of (f) producing a prioritized indication of maintenance required on the at least one component in dependence upon said analyzing in step (ci).

12. A system for assessing wall thinning rate of a containment system containing a substance and subject to erosion and corrosion, comprising:
   storage means for storing characteristic data and inspection data for at least one component of the containment system to be monitored;
   acquisition means for acquiring the inspection data including actual wall thickness of the at least one component; and
   evaluation means for automatically evaluating the inspection data based on the characteristic data to produce an assessment of the wall thinning rate of the at least one component.

13. A system as recited in claim 12, wherein the containment system includes a piping system measured using ultrasonic testing equipment,
   wherein the characteristic data includes at least one of a component identification number, a description of component structure, pipe size, nominal wall thickness, material properties, operating conditions, an inspection grid and a component location for the at least one component, and wherein said acquisition means comprises:

means for periodically acquiring the actual wall thickness of the at least one component from the ultrasonic testing equipment and an inspection identifier corresponding to the actual wall thickness; and means for storing the actual wall thickness in said storage means at locations determined in dependence upon the inspection identifier and the component identification number.

14. A system as recited in claim 13, wherein said evaluation means includes:

means for evaluating the wall thinning rate of the at least one component in dependence upon the actual wall thickness most recently acquired and stress calculated in dependence upon the characteristic data; and means for extrapolating from the inspection data acquired over a period of time for the at least one component to predict future wall thickness of the at least one component.

15. A system for assessing containment integrity of piping systems in a pressurized water nuclear reactor powered electricity generation plant, comprising:

storage means for storing characteristic data and inspection data for a plurality of components in the plant;

input means for inputting the characteristic data including component identification members, descriptions of component structure, pipe sizes, nominal wall thicknesses, material properties, locations of the components, operating conditions and inspection grids corresponding to the components;

acquisition means for repeatedly acquiring the inspection data, including actual wall thicknesses measured at a plurality of points on each of the components and for validating the inspection data by comparing the inspection data with predetermined ranges to identify errors and to identify any of the points which indicate excessive wall thinning; and evaluation means for automatically evaluating the inspection data in dependence upon the actual wall thicknesses most recently acquired and stress calculated in dependence upon the characteristic data and for extrapolating from the inspection data acquired over a period of time for each of the components to predict future wall thicknesses of the components.

* * * * *